(12) United States Patent
Lindhofer

(10) Patent No.: US 8,277,806 B2
(45) Date of Patent: Oct. 2, 2012

(54) USE OF TRIFUNCTIONAL BISPECIFIC AND TRISPECIFIC ANTIBODIES FOR THE TREATMENT OF MALIGNANT ASCITES

(75) Inventor: Horst Lindhofer, Gröbenzell (DE)

(73) Assignee: Trion Pharma GmbH, München (DE)

( * ) Notice: Subject to any disclaimer, the term of this patent is extended or adjusted under 35 U.S.C. 154(b) by 161 days.

(21) Appl. No.: 10/378,218

(22) Filed: Mar. 3, 2003

(65) Prior Publication Data
US 2003/0223999 A1 Dec. 4, 2003

Related U.S. Application Data

(63) Continuation of application No. PCT/EP01/10184, filed on Sep. 4, 2001.

(30) Foreign Application Priority Data

Sep. 4, 2000 (DE) .................................. 100 43 437

(51) Int. Cl.
*A61K 39/395* (2006.01)
(52) U.S. Cl. ............... 424/136.1; 424/130.1; 424/133.1; 424/138.1; 424/143.1; 424/144.1; 424/152.1; 424/155.1; 424/172.1; 424/174.1
(58) Field of Classification Search ............... 424/130.1, 424/133.1, 136.1, 141.1, 144.1, 152.1, 155.1, 424/172.1, 174.1
See application file for complete search history.

(56) References Cited

U.S. PATENT DOCUMENTS

| | | | | |
|---|---|---|---|---|
| 5,837,243 | A * | 11/1998 | Deo et al. ................ | 424/136.1 |
| 5,985,276 | A | 11/1999 | Lindhofer et al. | |
| 6,207,147 | B1 * | 3/2001 | Hiserodt et al. ........... | 424/93.1 |
| 6,551,592 | B2 * | 4/2003 | Lindhofer et al. ........ | 424/136.1 |
| 6,805,869 | B2 * | 10/2004 | Guo .......................... | 424/278.1 |
| 6,994,853 | B1 * | 2/2006 | Lindhofer et al. | |
| 7,018,632 | B2 * | 3/2006 | Lindhofer et al. | |
| 2002/0022017 | A1 * | 2/2002 | Yu ............................ | 424/93.21 |

FOREIGN PATENT DOCUMENTS

| | | |
|---|---|---|
| DE | 195 31 348 A1 | 2/1997 |
| DE | 197 10 497 C2 | 3/1998 |
| DE | 198 59 115 A1 | 3/2000 |
| DE | 198 59 110 A1 | 4/2000 |
| EP | 0 885 614 B1 | 12/1998 |
| WO | 00/18806 | 4/2000 |
| WO | WO 0018435 A1 * | 4/2000 |

OTHER PUBLICATIONS

Strauss et al. Clinical Cancer Research 5:171-180, 1999.*
Kroesen et al. Cancer Immunology Immunotherapy, 37:400-407, 1993.*
Zeidler et al. Journal of Immunology, 163(3):1246-1252, 1999.*
Lindhofer et al. Blood, 88(2):4651-4658, 1996.*
Weiner et al. Leukemia and Lymphoma, 16(3-4):199-207, 1995.*
Chaudry et al. British Journal of Cancer, 96(7):1013-1019, 2007.*
Lindhofer H. Biospektrum, 6(6):500-501, 2000, English translation.*
Fundamental Immunology, William E. Paul, M.D. ed., 3rd ed., p. 242, 1993.*
Demanet, C., Blood, 87(10): 4390-4398, 1998.*
Dr. Horst Lindhofer, "Neuartige trifunktionelle Antikorper befreien Stammzelltransplantate von residualen Tumorzellen," Biospektrum, vol. 6 ( No. 6), p. 500-501, (2000).
R. Zeidler et al., "The Fc-region of a new class of intact bispecific antibody mediates activation of accessory cells and NK cells and induces direct phagocytosis of tumour cells," British Journal of Cancer, vol. 83 ( No. 2), p. 261-266, ( Jul. 20, 2000).
H. Lindhofer et al., "Preferential Species-Restricted Heavy/Light Chain Pairing in Rat/Mouse Quadromas," The Journal of Immunology, vol. 155 ( No. 1), p. 219-225, ( Jul. 1, 1995).
Luo et al., "Significant Expression of Vascular Endothelial Growth Factor/Vascular Permeability Factor in Mouse Ascites Tumors," Cancer Research. vol. 58 pp. 2652-2660 (1998).
Zebrowski et al., "Markedly Elevated Levels of Vascular Endothelial Growth Factor in Malignant Ascites," Annals of Surgical Oncology. vol. 6, No. 4 pp. 373-378 (1999).
"Orthoclone Okt3 (Muromonab-CD3)—Warnings and Precautions," DrugLib.com pp. 1-8 (Accessed on May 11, 2012) <http://www.druglib.com/druginfo/orthoclone-okt3/warnings_perc...>.
Chatenoud, "OKT3-Induced Cytokine-Release Syndrome: Preventive Effect of Anti-Tumor Necrosis Factor Monoclonal Antibody," Transplantation Proceedings. vol. 25, No. 2, Supplement 1 pp. 47-51 (1993).
Haagen et al., "Interaction of human monocyte Fc gamma receptors with rat IgG2b. A new indicator for the Fc gamma RIIa (R-H131) polymorphism," Journal of Immunology. vol. 154 pp. 1852-1860 (1995).
Horvath, C.J., and Milton, M.N., "The TeGenero Incident and the Duff Report Conclusions: A Series of Unfortunate Events or an Avoidable Event?" Toxicologic Pathology, vol. 37, pp. 372-383 (2009). Mackey et al., "A phase II trial of triamcinolone hexacetanide for symptomatic recurrent malignant ascites," Journal of Pain Symptom Management. vol. 19 pp. 193-199 (2000).
Matthys et al., "Modification of the anti-CD3-induced cytokine release syndrome by anti-interferon-γ or anti-interleukin-6 antibody treatment: protective effects and biphasic changes in blood cytokine levels," European Journal of Immunology. vol. 23 pp. 2209-2216 (1993).
Ruf, P., and Lindhofer, H., "Induction of a long-lasting antitumor immunity by a trifunctional bispecific antibody," Blood. vol. 98, No. 8 pp. 2526-2534 (2001).
Suntharalingam et al., "Cytokine Storm in a Phase I Trial of the Anti-CD28 Monoclonal Antibody TGN1412," The New England Journal of Medicine. vol. 355 pp. 1018-1028 (2006).

* cited by examiner

*Primary Examiner* — Alana Harris Dent
*Assistant Examiner* — Anne Holleran
(74) *Attorney, Agent, or Firm* — Jenkins, Wilson, Taylor & Hunt, P.A.

(57) ABSTRACT

The invention describes the use of a pharmaceutical preparation containing a trifunctional bispecific and/or trispecific having the following properties:
a) binding to a T cell;
b) binding to at least an antigen on a tumor cell associated with malignant ascites and/or pleural effusion;
c) binding, by its Fc portion (in the case of bispecific antibodies) or by a third specificity (in the case of trispecific antibodies), to Fc receptor-positive cells for the destruction of the tumor cells in the treatment of malignant ascites and/or pleural effusion.

14 Claims, 5 Drawing Sheets

Destruction of tumor cells in the ascites liquid
by the bsab anti-CD3Xanti-EpCAM
(detection by RT-PCR)

Peritoneal lavages at different time points during removab® treatment

RNA preparation

RT and *nested* PCR

Disappearance of the tumor cells in the ascites liquid after bsab administaration

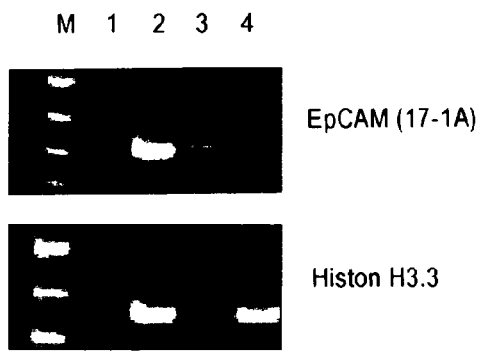

EpCAM (17-1A)

Histon H3.3

M = DNA standard
1 = Control
2 = Ascites Day 0
3 = Lavage Day 8 after 80 µg bsAk
4 = Lavage Day 15 after 160 µg bsAk

FIG. 3

USE OF TRIFUNCTIONAL BISPECIFIC AND TRISPECIFIC ANTIBODIES FOR THE TREATMENT OF MALIGNANT ASCITES

RELATED APPLICATIONS

This application is a continuation of PCT patent application number PCT/EP01/10184, filed Sep. 4, 2001, which claims priority to German patent application number 10043437.1, filed Sep. 4, 2000, the disclosures of each of which are incorporated herein by reference in their entirety.

TECHNICAL FIELD

The invention relates to the use of a pharmaceutical preparation containing trifunctional bispecific antibodies and/or trispecific antibodies for the destruction of the tumor cells associated with malignant ascites and/or pleural effusion in order to treat malignant ascites or pleural effusion.

Malignant ascites may be caused by a plurality of primary tumors such as e.g. breast cancer, ovarian carcinoma or the gastrointestinal carcinomas. Although ascites is detected in a high percentage of patients already during the first manifestation of a tumor disease, it is an indication of a progressive disease.

The present options for a therapy of ascites include puncture, local chemotherapy, or diuretic treatment. All these options have dramatic disadvantages; thus, puncture only leads to a short-term alleviation and has to be repeated after 9.5 days on average (Mackey et al., J. Pain Symptom Manage, 19:193, 2000). Chemotherapy, however, can only be successful in patients who have not already developed chemotherapy-resistant tumor cells which unfortunately is often the case. In this respect, there is an enormous need for an improvement of the clinical treatment options in the case of ascites.

The situation is similar in the case of tumor cell-induced pleural effusion. Pleural effusion is an accumulation of liquid in the pleural space which may form again after a puncture. Since one of the causes of pleural effusion is the presence of tumor cells within this body compartment, destruction of the tumor cells is an important prerequisite to inhibit reformation of the pleural effusion. This means that the problems associated with malignant ascites and tumor cell-based pleural effusion and therefore the respective approaches to a solution are very similar.

SUMMARY OF THE INVENTION

It is an object of the invention to provide a novel means for the treatment of malignant ascites and for the treatment of pleural effusion which overcomes the disadvantages of the prior art and, particularly, offers a noticeable alleviation to the patient.

According to the invention, this object has been achieved by a pharmaceutical preparation containing a trifunctional bispecific and/or trispecific antibody having the following properties:
a) binding to a T cell;
b) binding to at least an antigen on a tumor cell associated with malignant ascites and/or pleural effusion;
c) binding, by its Fc portion (in the case of bispecific antibodies) or by a third specificity (in the case of trispecific antibodies), to Fc receptor-positive cells
for the destruction of the tumor cells in the treatment of malignant ascites and/or pleural effusion.

Further embodiments of the present invention may be seen from the accompanying claims as well as the following description. It has to be pointed out that the invention is not limited to the preferred embodiments and the Examples mentioned below. In contrast, those skilled in the art in the frame of their technical knowledge may modify the invention in the scope of the accompanying claims in connection with the description without departing from the invention.

BRIEF DESCRIPTION OF THE DRAWINGS

The accompanying Figures serve to further illustrate the present invention. The Figures show:

FIG. 3: Destruction of residual tumor cells after CD3× EpCAM treatment by means of RT PCR;

DETAILED DESCRIPTION OF THE INVENTION

Figure 1:
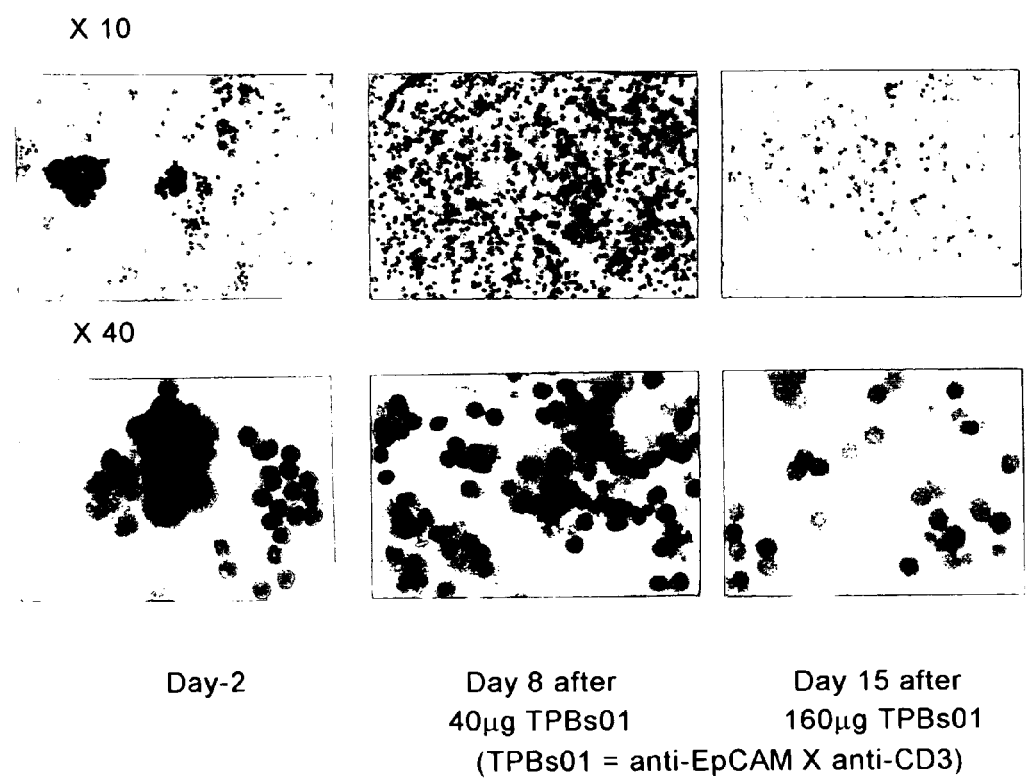
FIG. 1: Elimination of EpCAM+ tumor cells and proliferation of immune cells in the ascites under bsab therapy.

Trifunctional bispecific and trispecific antibodies and different fields of use of these antibodies are known from the prior art. Reference is made in this respect to DE 198 44 157.6 as well as DE 199 25 586. Although these state of the art documents describe the use of bispecific and trispecific antibodies having the three features a, b, and c for anti-tumor immunization, a direct treatment of the tumors by destruction of the tumor cells which goes beyond induction of an immunity is not described in these documents. These documents in particular do not disclose that a very specific partial area of the extraordinarily broad spectrum of tumor diseases, namely malignant ascites but also pleural effusion, may be treated by trifunctional bispecific and trispecific antibodies having the features listed above in a highly efficient and unexpected manner. Furthermore, a successful treatment has already been achieved in two clinical patients suffering form a final tumor disease (cf. Examples 1 and 2).

The pharmaceutical preparation has been designed to achieve at least a primary immunization by destruction of the tumor cells. For this purpose, the pharmaceutical preparation containing the trifunctional antibodies described in more detail below is administered in several doses. The first dose is selected to test a reaction to foreign proteins of the patient in response to the antibodies administered. The second dose is preferably selected to achieve activation and proliferation of the patient's immune cells. A third dose and further doses are selected to particularly achieve destruction of the tumor cells.

Administration of the first dose is carried out in an amount of 1 to 20 µg, preferably 5 to 10 µg of antibody to test for allergic reactions. Administration of the second dose is performed in an amount of 20 to 100 µg, preferably 80 µg, further preferred 30 to 60 µg of antibody. The administration of the third dose and of any further dose is performed in an amount of more than 80 µg, preferably 100 to 500 µg, further preferred 100 to 300 µg of antibody. It should be understood by those skilled in the art that these amounts are only guide numbers which may vary between patients and antibodies. It is within the skill of those working in the medical field, however, to appropriately select the amount of antibody to be employed in individual cases.

The number of applications preferably is an application of one dose 3 to 8 times, preferably 3 to 6 times. The administration is carried out in certain intervals, and preferably intervals of 48 to 72 hours are selected. Preferably, between individual applications an interval of 2-3 days plus/minus several hours is selected. The applications are preferably continued over a period of 12-14 days. The period is selected in a way that no further antibody doses will be administered from the point when first immune reactions against the antibody protein are observed. If a mouse antibody is used then for example the HAMA (human anti-mouse antibody) reaction will be determined which generally is initiated after 16 to 21 days, in some patients earlier, in others later or not at all.

As detailed above, malignant ascites is particularly frequent in a plurality of primary tumors such as breast cancer, ovarian carcinoma and gastrointestinal carcinomas. Such tumor diseases are treated by first resecting the tumor tissue by surgery and subsequent chemotherapy. In a preferred embodiment of the invention the patient's immune cells are obtained by apheresis. This apheresis product is an accumulation of blood cells which particularly does not contain erythrocytes. Contained are especially T cells, macrophages, monocytes, NK cells, dendritic cells, granulocytes, and B cells. The preparation of the apheresis product must be particularly carried out prior to the first chemotherapy to ensure integrity of the immune cells which are almost always affected by the chemotherapeutics.

In one embodiment of the invention, the patient is not only treated by the trifunctional bispecific and/or trispecific antibodies but, in the frame of a secondary immunization, also receives in addition inactivated autologous and/or allogenic tumor cells and autologous immune cells. The autologous immune cells preferably are T lymphocytes and accessory cells, for example monocytes, macrophages and dendritic cells. These cells are for example contained in PBMC (peripheral blood mononuclear cells) which may be obtained for example from heparinized blood via Ficoll density gradient centrifugation. It is also possible, however, to employ subfractions, e.g. only T lymphocytes and dendritic cells or macrophages, respectively, etc. In a preferred embodiment the autologous immune cells are the apheresis cells which are employed in an admixture together with the antibody and the inactivated autologous or allogenic tumor cells.

For successful immunization it is further advantageous to select the amount of tumor cells administered in a suitable manner. Thus, it has been shown in experiments with the murine tumor model that too low a number of tumor cells does not bring about the desired immunization success. Too high a number of tumor material, however, may have an disadvantageous effect since for example tolerance phenomena may arise. If these results are applied to the situation in the patient, this would mean that it is advantageous for a successful immunization to administer a defined amount of tumor material in the correct spatial context together with amount of antibodies which has also been defined. Although successful immunization will also be achieved if one of these parameters has not been optimized, particularly good results are achieved, however, if the amounts of the antibody and the amount of tumor material as well as the spatial context have been matched and optimized.

Considering what has been explained above, in the case of too low a number of tumor cells only an insufficient immune protection can be established. Therefore, it is required for a complete success of immunization to immunize with a defined number of inactivated tumor cells and a defined amount of bispecific and/or trispecific antibodies. The respective numbers may be determined by those skilled in the art by way of experiments.

The tumor cells are preferably administered in an amount of $10^5$-$10^8$ cells per application while a cell number of about $10^7$ has been found to be preferable. Prior to their reapplication, the tumor cells have been treated as detailed above so that their survival after reapplication is inhibited while they optionally may additionally be subjected to heat pretreatment.

The tumor cells are obtained from the tumor material of the patient to be treated. For example, the tumor material will be worked up to yield a single cell suspension by enzymatic treatment, preferably by collagenase treatment. It is important that the tumor cells are as undamaged as possible. Tumor cell lysates have been found unsuitable. Prior to their application the tumor cells are treated to exclude survival of the tumor cells in the patient. Therefore, the tumor cells are treated in a manner known per se, e.g. by irradiation or treatment with chemical agents. By this treatment, especially the outer structure of the tumor cell should remain unaffected to retain the recognition pattern for the antibodies.

Preferably, γ-irradiation is used for irradiation, which preferably is carried out at a dose of 20 to 200 Gy. For a chemical treatment, mitomycin C has been found particularly successful.

A further improvement of the immunogenicity of the tumor cells may be achieved by subjecting them to a heat pretreatment prior to infusion. The preferred temperature is in the range of 41 to 45° C. while a range of 41 to 42° C. is preferred. The optimum may be determined by experimentation. Preferred results are achieved particularly at a temperature of about 41.8° C. The period for the heat pretreatment generally is 1 to 6 hours, preferably about 3 hours. The period as well as the temperature which may be optimally employed are dependent on the type of tumor to be treated. The respective optimal values may be determined by those skilled in the art by way of experiments.

Administration of the single doses generally is performed in a way that an intraperitoneal application form is chosen wherein the antibodies are infused into the patient to achieve a primary immunization, i.e. destruction of the tumor cells. Administration of the doses for secondary immunization generally is carried out by local application, for example intradermally, subcutaneously or intramuscularly. It may also be performed intraperitoneally or intravenously.

If together with the trifunctional antibodies also the inactivated autologous and/or allogenic tumor cells and the autologous immune cells are administered to achieve a secondary immunity the following amounts are preferably used:
a) 1-200×$10^6$ inactivated tumor cells, preferably 1-100×$10^6$ inactivated tumor cells
b) 10-500×$10^6$ immune cells, preferably 50-200×$10^6$ immune cells
c) 1-10 μg trifunctional bispecific antibodies or trispecific antibodies, preferably 2-5 μg antibodies.

As already detailed above, however, those skilled in the art will choose the respective amount and the site of application to ensure an optimal therapeutic success.

The pharmaceutical preparation provided according to the invention is for example present in an isotonic saline. Other components may be for example stabilizing agents such as Tween 80 or buffer solutions.

For treatment, preferably intact trifunctional bispecific and/or trispecific antibodies are used. The treatment not only achieves the surprising direct destruction of the tumor cells described above but an immunity is also induced which is directed against the tumor.

By "intact antibodies" there are meant those antibodies having a functional Fc portion. Preferably those are heterologous antibodies, i.e. they are combined of heavy immune globulin chains of different subclasses (combinations, also fragments) and/or different origin (species).

Besides the features a, b, and c described above, in preferred embodiments of the invention the antibodies employed also show the additional features d and e:
d) activates the Fc receptor-positive cell by its binding to the Fc receptor-positive cell whereby the expression of cytokines and/or of co-stimulatory antigens is initiated or increased;
e) the co-stimulatory antigens and/or cytokines transfer to the T cell at least one $2^{nd}$ activation signal which is required for physiological activation of the T cell, this activation being indicated by an up-regulation of activation markers, a destruction of the tumor cell and/or a proliferation of the T cell.

In the following, the invention will be described particularly using bispecific antibodies as an example. The results, however, can also be achieved with trispecific antibodies.

The antibodies useful according to the present invention are capable of activating the Fc receptor-positive cell whereby the expression of cytokines and/or co-stimulatory antigens is initiated or increased.

In the case of the trispecific antibodies, binding to the Fc receptor-positive cells preferably occurs for example via the Fc receptor of Fc receptor-positive cells or alternatively via other antigens on Fc receptor-positive cells (antigen-presenting cells) such as the mannose receptor.

By means of the combination and the way of application of the intact, preferably heterologous bispecific and/or trispecific antibodies of the present invention, besides a treatment of the ascites and the pleural effusion by direct destruction of the tumor cells also an anti-tumor immunity, preferably a long-lasting anti-tumor immunity is developed in the patient. The administration is preferably performed in a patient after treatment of the primary tumor, preferably in patients in a minimal residual disease (MRD) situation. In patients with a low amount of residual tumor cells in whom, however, the risk of a recurrency may be high, the application of the pharmaceutical preparation described according to the present invention is especially successful.

The heterologous bispecific and/or trispecific antibodies which may be used according to the present invention are known per se. For example they have been described in Lindhofer et al., Blood, 88:4651, 1996; or Lindhofer et al., J. Immunology, 155:219, 1995.

On the tumor cell, an up-regulation of MHC I as well as an activation of the intracellular processing machinery (proteasome complex) occurs due to the release of cytokines (such as INF-γ and TNF-α) in the direct vicinity of the tumor cell. The cytokines are released due to bispecific antibody-mediated activation of T cells and accessory cells. This means that due to the intact bsab not only tumor cells are destroyed or phagocytized but indirectly also the anti-tumor immunogenicity is increased.

Activation of the Fc receptor-positive cell by the bsab is dependent on the subclass or the subclass combination, respectively, of the bsab. As demonstrated in in vitro experiments, for example, bsabs of the subclass combination mouse-IgG2a/rat-IgG2b are capable of binding to and simultaneously activating Fc receptor-positive cells resulting in an up-regulation or new formation (expression), respectively, of co-stimulatory antigens such as CD40, CD80, or CD86 on the cell surface of these cells. (Zeidler et al., J. Immunol., 163: 1246, 1999). In contrast, bsabs of the subclass combination mouse-IgG1/rat-IgG2b are able to bind to Fc receptor-positive cells (Haagen et al., J. Immunology, 1995, 154: 1852-1860) but obviously are unable to activate these cells to a comparable extent (Gast et al., Cancer Immunol. Immunother., 1995, 40: 390).

While the intact bsab simultaneously binds to and activates the T cell with one binding arm (e.g. to CD3 or CD2), co-stimulatory signals from the Fc receptor-positive cell bound to the Fc portion of the bsab may be transferred to the T cell. This means that only the combination of T cell activation via one binding arm of the bsab and simultaneous transfer of co-stimulatory signals from the Fc receptor-positive cell to the T cell results in an efficient T cell activation. Also, tumor-specific T cells which have been insufficiently activated at the tumor cell and therefore are anergic may be reactivated by the treatment with intact bispecific antibodies or trispecific antibodies according to the present invention.

Another important aspect in the induction of an anti-tumor immunity is possible phagocytosis, processing and presentation of tumor components by the accessory cells (monocytes/macrophages, or dendritic cells) which have been recruited and activated by the bsab. By this classical mechanism of presentation of antigens both tumor-specific CD4- as well as CD8-positive cells may be generated. Moreover, tumor-specific CD4 cells play an important role in the induction of a humoral immune response in the context of T/B cell cooperation.

Bispecific and trispecific antibodies are able to bind to the T cell receptor complex of the T cell with one binding arm and to tumor-associated antigens on the tumor cell with the second binding arm. Thereby, they activate T cells which destroy the tumor cells by releasing cytokines or by apoptosis-mediating mechanisms. Moreover, there seems to be the possibility that in the frame of activation by bispecific antibodies T cells recognize tumor-specific antigens via their receptor and thereby a long-lasting immunization is initiated. Of particular importance in this respect is the intact Fc portion of the bispecific or trispecific antibody mediating the binding to accessory cells such as monocytes/macrophages and dendritic cells and causing them to become cytotoxic themselves and/or to concomitantly transfer important co-stimulatory signals to the T cell. Obviously, in this manner under certain circumstances a T cell response may be induced against so far unknown tumor-specific peptides.

By redirection of possibly anergized tumor-specific T cells to tumor cells by means of bispecific and/or trispecific antibodies and simultaneous co-stimulation of such T cells by accessory cells binding to the Fc portion of the bispecific or trispecific antibody the anergy of cytotoxic T cells (CTLs) could be abolished. This means that a T cell tolerance against the tumor existing in the patient may be abolished by means of intact heterologous bispecific and/or trispecific antibodies and, thus, a long-term anti-tumor immunity may be induced.

This last issue is supported by initial in vivo data from experiments with mice indicating a long-term anti-tumor immunity of this kind after treatment with a syngeneic tumor and intact bsabs. In these experiments, a total of 14 out of 18 animals which could be successfully treated with bsabs following a first tumor injection survived a second tumor injection carried out 144 days after the first injection—without an additional bsab administration.

Preferably, the antibodies employed according to the present invention are capable of reactivating tumor-specific antigens being in the anergic state. Furthermore, they are capable of inducing tumor-reactive complement-binding antibodies and therefore inducing a humoral immune response.

Binding to the T cell preferably takes place via CD3, CD2, CD4, CD5, CD6, CD8, CD28, CD40L and/or CD44. The Fc receptor-positive cells at least have one Fcγ receptor type I or III.

Antibodies which may be employed according to the present invention are able to bind to monocytes, macrophages, dendritic cells, "natural killer" cells (NK cells) and/or activated neutrophils being Fcγ receptor I and/or III-positive cells (Zeidler, 1999, Zeidler 2000 loc. cit.)

The antibodies which may be employed according to the invention have the effect that the expression of CD40, CD80, CD86, ICAM-1, and/or LFA-3 as co-stimulatory antigens, or/and the secretion of cytokines by the Fc receptor-positive cell is initiated or increased. Preferably, the cytokines are IL-1, IL-2, IL-4, IL-6, IL-8, IL-12, INF-γ and/or TNF-α.

The bispecific antibodies which may be employed according to the present invention are for example:
an anti-CD3 X anti-tumor-associated antigen antibody and/or anti-CD4 X anti-tumor-associated antigen antibody and/or anti-CD5 X anti-tumor-associated antigen antibody and/or anti-CD6 X anti-tumor-associated antigen antibody and/or anti-CD8 X anti-tumor-associated antigen antibody and/or anti-CD2 X anti-tumor-associated antigen antibody and/or anti-CD28 X anti-tumor-associated antigen antibody and/or anti-CD40L X anti-tumor-associated antigen antibody and/or anti-CD44 X anti-tumor-associated antigen antibody.

The trispecific antibodies which may be employed according to the present invention preferably are:
an anti-CD3 X anti-tumor-associated antigen antibody and/or anti-CD4 X anti-tumor-associated antigen antibody and/or anti-CD5 X anti-tumor-associated antigen antibody and/or anti-CD6 X anti-tumor-associated antigen antibody and/or anti-CD8 X anti-tumor-associated antigen antibody and/or anti-CD2 X anti-tumor-associated antigen antibody and/or anti-CD28 X anti-tumor-associated antigen antibody and/or anti-CD40L X anti-tumor-associated antigen antibody and/or anti-CD44 X anti-tumor-associated antigen antibody.

The trispecific antibodies which may be used according to the present invention at least have one T cell binding arm, one tumor cell binding arm as well as an arm binding to Fc receptor-positive cells. This last binding arm may be an anti-Fc receptor binding arm or a mannose receptor binding arm.

Preferably, the bispecific antibody is a heterologous intact rat/mouse bispecific antibody.

By means of the bispecific and trispecific antibodies which may be used according to the present invention, T cells are activated and redirected against the tumor cells. Preferably used heterologous intact bispecific antibodies are selected from one or more of the following isotype combinations:
rat-IgG2b/mouse-IgG2a,
rat-IgG2b/mouse-IgG2b,
rat-IgG2b/mouse-IgG3;
rat-IgG2b/human-IgG1,
rat-IgG2b/human-IgG2,
rat-IgG2b/human-IgG3[oriental allotype G3m(st)=binding to protein A],
rat-IgG2b/human-IgG4;
rat-IgG2b/rat-IgG2c;
mouse-IgG2a/human-IgG3[caucasian allotypes G3m(b+g)=no binding to protein A, in the following indicated as *]

mouse-IgG2a/mouse-[VH-CH1,VL-CL]-human-IgG1-[hinge]-human-IgG3*-[CH2-CH3]
mouse-IgG2a/rat-[VH-CH1,VL-CL]-human-IgG1-[hinge]-human-IgG3*-[CH2-CH3]
mouse-IgG2a/human-[VH-CH1,VL-CL]-human-IgG1-[hinge]-human-IgG3*-[CH2-CH3]
mouse-[VH-CH1,VL-CL]-human-IgG1/rat-[VH-CH1,VL-CL]-human-IgG1-[hinge]-human-IgG3*-[CH2-CH3]
mouse-[VH-CH1,VL-CL]-human-IgG4/rat-[VH-CH1,VL-CL]-human-IgG4-[hinge]-human-IgG4[N-terminal region of CH2]-human-IgG3*[C-terminal region of CH2: >aa position 251]-human-IgG3*[CH3]
rat-IgG2b/mouse-[VH-CH1,VL-CL]-human-IgG1-[hinge-CH2-CH3]
rat-IgG2b/mouse-[VH-CH1,VL-CL]-human-IgG2-[hinge-CH2-CH3]
rat-IgG2b/mouse-[VH-CH1,VL-CL]-human-IgG3-[hinge-CH2-CH3, oriental allotype]
rat-IgG2b/mouse-[VH-CH1,VL-CL]-human-IgG4-[hinge-CH2-CH3]
human-IgG1/human-[VH-CH1,VL-CL]-human-IgG1-[hinge]-human-IgG3*-[CH2-CH3]
human-IgG1/rat-[VH-CH1,VL-CL]-human-IgG1-[hinge]-human-IgG4[N-terminal region of CH2]-human-IgG3*[C-terminal region of CH2: >aa position 251]-human-IgG3*[CH3]
human-IgG1/mouse-[VH-CH1,VL-CL]-human-IgG1-[hinge]-human-IgG4[N-terminal region of CH2]-human-IgG3*[C-terminal region of CH2: >aa position 251]-human-IgG3*[CH3]
human-IgG1/rat-[VH-CH1,VL-CL]-human-IgG1-[hinge]-human-IgG2[N-terminal region of CH2]-human-IgG3*[C-terminal region of CH2: >aa position 251]-human-IgG3*[CH3]
human-IgG1/mouse-[VH-CH1,VL-CL]-human-IgG1-[hinge]-human-IgG2[N-terminal region of CH2]-human-IgG3*[C-terminal region of CH2: >aa position 251]-human-IgG3*[CH3]
human-IgG1/rat-[VH-CH1,VL-CL]-human-IgG1-[hinge]-human-IgG3*-[CH2-CH3]
human-IgG1/mouse-[VH-CH1,VL-CL]-human-IgG1-[hinge]-human-IgG3*-[CH2-CH3]
human-IgG2/human-[VH-CH1,VL-CL]-human-IgG2-[hinge]-human-IgG3*-[CH2-CH3]
human-IgG4/human-[VH-CH1,VL-CL]-human-IgG4-[hinge]-human-IgG3*-[CH2-CH3]
human-IgG4/human-[VH-CH1,VL-CL]-human-IgG4-[hinge]-human-IgG4[N-terminal region of CH2]-human-IgG3*[C-terminal region of CH2: >aa position 251]-human-IgG3*[CH3]
mouse-IgG2b/rat-[VH-CH1,VL-CL]-human-IgG1-[hinge]-human-IgG3*-[CH2-CH3]
mouse-IgG2b/human-[VH-CH1,VL-CL]-human-IgG1-[hinge]-human-IgG3*-[CH2-CH3]
mouse-IgG2b/mouse-[VH-CH1,VL-CL]-human-IgG1-[hinge]-human-IgG3*-[CH2-CH3]
mouse-[VH-CH1,VL-CL]-human-IgG4/rat-[VH-CH1,VL-CL]-human-IgG4-[hinge]-human-IgG4-[CH2]-human-IgG3*-[CH3]
human-IgG1/rat-[VH-CH1,VL-CL]-human-IgG1-[hinge]-human-IgG4-[CH2]-human-IgG3*-[CH3]
human-IgG1/mouse-[VH-CH1,VL-CL]-human-IgG1-[hinge]-human-IgG4-[CH2]-human-IgG3*-[CH3]
human-IgG4/human-[VH-CH1,VL-CL]-human-IgG4-[hinge]-human-IgG4-[CH2]-human-IgG3*-[CH3]

The antibodies which may be used according to the present invention preferably are monoclonal, chimeric, recombinant, synthetic, semi-synthetic, or chemically modified intact antibodies having for example Fv, Fab, scFv, or F(ab)$_2$ fragments.

Preferably, antibodies or derivatives or fragments of humans are used, or those which have been modified to be suitable for the use in humans (so-called "humanized antibodies") (see for example Shalaby et al., J. Exp. Med. 175 (1992), 217; Mocikat et al., Transplantation 57 (1994), 405).

The preparation of the different types of antibodies and antibody fragments mentioned above is well-known to the skilled artisan. The preparation of monoclonal antibodies, preferably of those originating in mammals, e.g. human, rat, mouse, rabbit, or goat, can be performed using conventional methods as those described for example in Köhler und Milstein (Nature 256 (1975), 495), in Harlow and Lane (Antibodies, A Laboratory Manual (1988), Cold Spring Harbor) or in Galfré (Meth. Enzymol. 73 (1981), 3) or in DE 195 31 346.

It is further possible to prepare the antibodies described by means of recombinant DNA technology according to techniques known to those skilled in the art (see Kurucz et al., J. Immunol. 154 (1995), 4576; Hollinger et al., Proc. Natl. Acad. Sci. USA 90 (1993), 6444).

The preparation of antibodies having two different specificities, the so-called bispecific antibodies, can be performed on the one hand using recombinant DNA technology but on the other hand also by the so-called hybrid hybridoma fusion technique (see for example Milstein et al., Nature 305 (1983), 537). For this purpose, hybridoma cell lines each producing antibodies having one of the desired specificities are fused and cellular clones (quadromas) producing antibodies having both specificities are identified and isolated.

The problem underlying the present invention can be solved using both bispecific and trispecific antibodies which preferably exhibit the properties and effects characterized. In the following, the preparation of antibodies showing two and three specificities is described in more detail. To provide such bispecific and trispecific antibodies is known from the prior art, and references describing such techniques of preparation are incorporated herein by reference in their entirety.

The preparation of antibodies exhibiting three specificities, so-called trispecific antibodies, by which the problem underlying the present invention can also be solved may be for example carried out by coupling to one of the IgG heavy chains of a bispecific antibody a third antigen binding site having an additional specificity, e.g. in the form of a "single chain variable fragment" (scFv). The scFv may be coupled for example using a

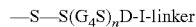

to one of the heavy chains (S=serine, G=glycine, D=aspartate, I=isoleucine).

In an analogous manner trispecific F(ab)$_2$ constructs may be prepared by replacing the CH2-CH3 regions of the heavy chain of one specificity of a bispecific antibody by an scFv having a third specificity while the CH2-CH3 regions of the heavy chain having the other specificity are removed for example by insertion of a stop codon (at the end of the "hinge" region) into the coding gene, e.g. by homologous recombination.

It is also possible to prepare trispecific scFv constructs. For this purpose three VH-VL regions representing three different specificities are arranged behind each other in series.

According to the present invention there are for example used intact bispecific antibodies. Intact bispecific antibodies are composed of two antibody semi-molecules (each having a H and a L immunoglobulin chain) each of which represents one specificity which additionally like normal antibodies have an Fc portion performing the well-known effector functions. They are preferably prepared using the quadroma technology. This method of preparation is described exemplarily in DE-A-44 19 399. For complete disclosure this document is incorporated by reference in its entirety also with respect to a definition of bispecific antibodies. It should be understood, however, that also other methods of preparation may be employed if they lead to the intact bispecific antibodies according to the above definition which are required by the present invention.

For example, intact bispecific antibodies may be produced in a sufficient amount using a newly developed method of preparation (Lindhofer et al., J. Immunology 1995, 155: 219). The combination of 2 bispecific antibodies directed against 2 different tumor-associated antigens (e.g. c-erb-B2, and Ep-CAM) on the mammary carcinoma cells minimizes the risk that tumor cells expressing only one antigen would remain unrecognized.

Further advantages of intact bsabs having the ability of redirecting T cells over the above-mentioned bsF(ab')2 fragments may be detailed as follows:

1. It is possible for Fc receptor-positive cells to bind to intact bsabs and to contribute on the one hand directly to tumor destruction via ADCC (antibody-dependent cell-mediated cytotoxicity) and on the other hand to T cell activation as explained in more detail above.
2. By intact T cell-redirecting bsabs also anergized tumor-specific T cells are recruited to the tumor cell which according to the invention may be reactivated directly at the tumor site. This may not be achieved by an bsF(ab')2 fragment having the specificities anti-CD64 X anti-tumor-associated antigen.

Binding of the bsab to Fcγ-RI has two essential advantages with regard to an optimal anti-tumor effectiveness:

(1) Fcγ-RI-positive cells have the ability to eliminate tumor cells by ADCC and, thus, are able to contribute synergistically to the anti-tumor effect of the cytotoxic T cells recruited to the tumor cell by the bsab.
(2) FcγRI-positive cells (such as monocytes/makrophages/dendritic cells) are able to provide important co-stimulatory signals similar to those involved in antigen presentation to the T cell and, thereby, to prevent anergizing of the T cell. Furthermore, because of the intact bsab-mediated interaction of T cell with accessory cell and tumor cell there can be stimulated as a desired by-product even T cells the T cell receptor of which recognizes tumor-specific peptides (presented via MHC antigens on the tumor cell). In this constellation, the co-stimuli necessary for correct activation of the T cell would be provided by the accessory cell (such as the monocyte). Thus, besides the direct, T cell receptor-independent bsab-mediated tumor destruction the antibody of the present invention should also be able to activate and generate tumor-specific T cells which after degradation of the bsab continue to patrol in the patient. This means that similar to gene-therapeutical approaches (e.g. by incorporation of co-stimulatory antigens such as B-7 into the tumor cell) the tumor tolerance in the patient may be abolished by means of intact bsabs.

As could be surprisingly demonstrated in two patients, the immune therapy of tumors by means of trifunctional bispecific antibodies can also be therapeutically used in the treatment of ascites.

In one patient suffering from ovarian carcinoma, the new formation of ascites following treatment with bsab could be inhibited for a period of 6 months. In this case also the complete destruction of the tumor cells present in the ascites liquid could be confirmed.

Example 1

A patient with ovarian carcinoma first underwent a peritoneum puncture, then ascites liquid (700 ml) was removed and the cells contained therein were analyzed. As shown in FIG. 1 the tumor cells could be unambiguously identified already by visual inspection due to their morphology. In addition, anti-EpCAM peroxidase staining was performed.

Counting of the cells in the ascites prior to treatment gave a ratio of about 50:50 of tumor cells to immune cells.

Figure 2:
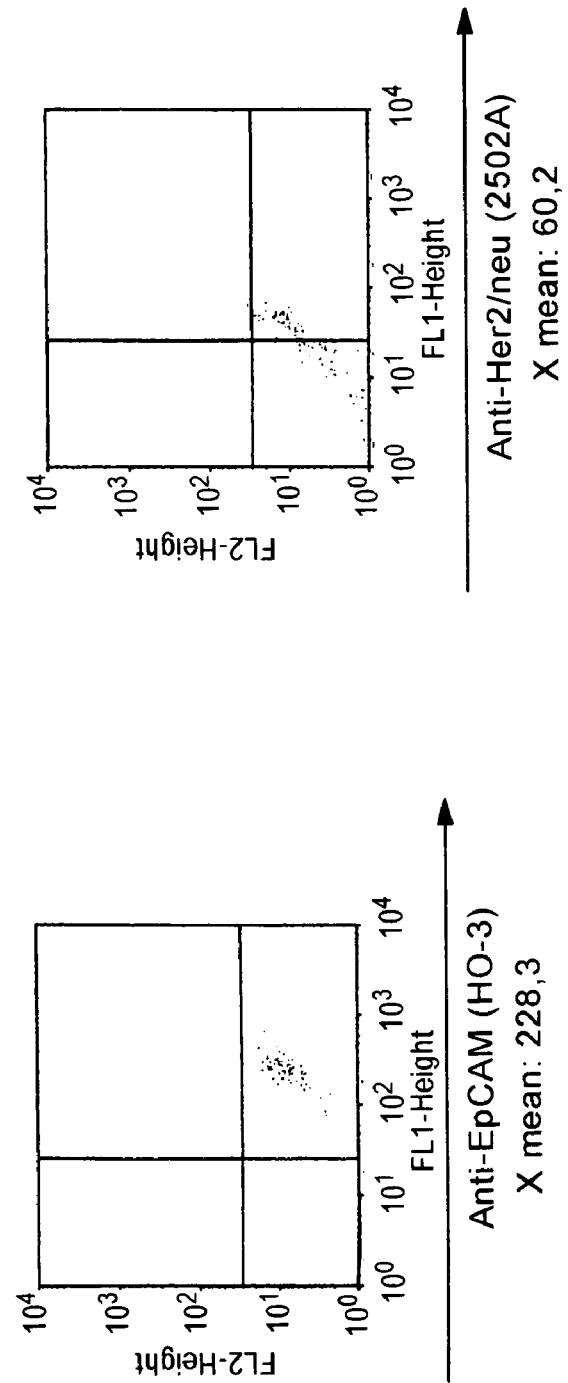
FIG. 2: FACS analysis of tumor cells for surface antigens.

The flow cytometric analysis revealed a strong positivity of the tumor cells for the EpCAM (epithelial cell adhesion molecule, Balzar et al., Mol. Cell. Biol., 18:4833, 1998) surface antigen as well as a weaker expression of the tumor-associated surface antigen Her2/neu (FIG. 2).

To exclude the possibility of a reaction to foreign protein, first 10 µg of TPBS03 REXOMAB bsab (anti-Her2/neu X anti-CD3; isotype combination mouse IgG2a X rat IgG2b) were infused intraperitoneally by means of a perfusor syringe over 8 h. The precise application is presented in Table 1.

TABLE 1

Dose regimen

| Day | Bispecific Antibody | Dose |
|---|---|---|
| 1 | CD3xHer2/neu | 10 µg |
| 4 | CD3xEpCAM | 10 µg |
| 7 | CD3xEpCAM | 40 µg |
| 9 | CD3xEpCAM | 80 µg |
| 11 | CD3xEpCAM | 160 µg |
| 15 | CD3xEpCAM + CD3xHer2/neu | 200 µg + 50 µg |

A first change could be observed 1 day after the 40 µg infusion. At this point a peritoneal lavage was performed and the cells contained therein were analyzed revealing that the ratio of immune cells to tumor cells had improved to a value of 3:1.

Surprisingly, on day 11 immediately prior to the 160 µg infusion only occasional tumor cells could be found. The ratio of immune cells to tumor cells had changed dramatically to a value of 330:1.

In the third peritoneal lavage on day 15 after the administration of 160 µg and immediately prior to the 250 µg infusion no more tumor cells could be detected (FIG. 1). This result could be confirmed using a particularly sensitive nested EpCAM RT PCR (FIG. 3).

It should be pointed out that during treatment no severe side effects occurred. Only after the highest dose of 250 µg bsab a short-term fever (38.6° C.) was observed.

In the patient, no new formation of the ascites liquid was observed over a period of 6 months and no further puncture had to be performed. This is remarkable because the disease stage of this patient at the beginning of immune therapy was very advanced and liver metastases already existed.

Example 2

Figure 4:
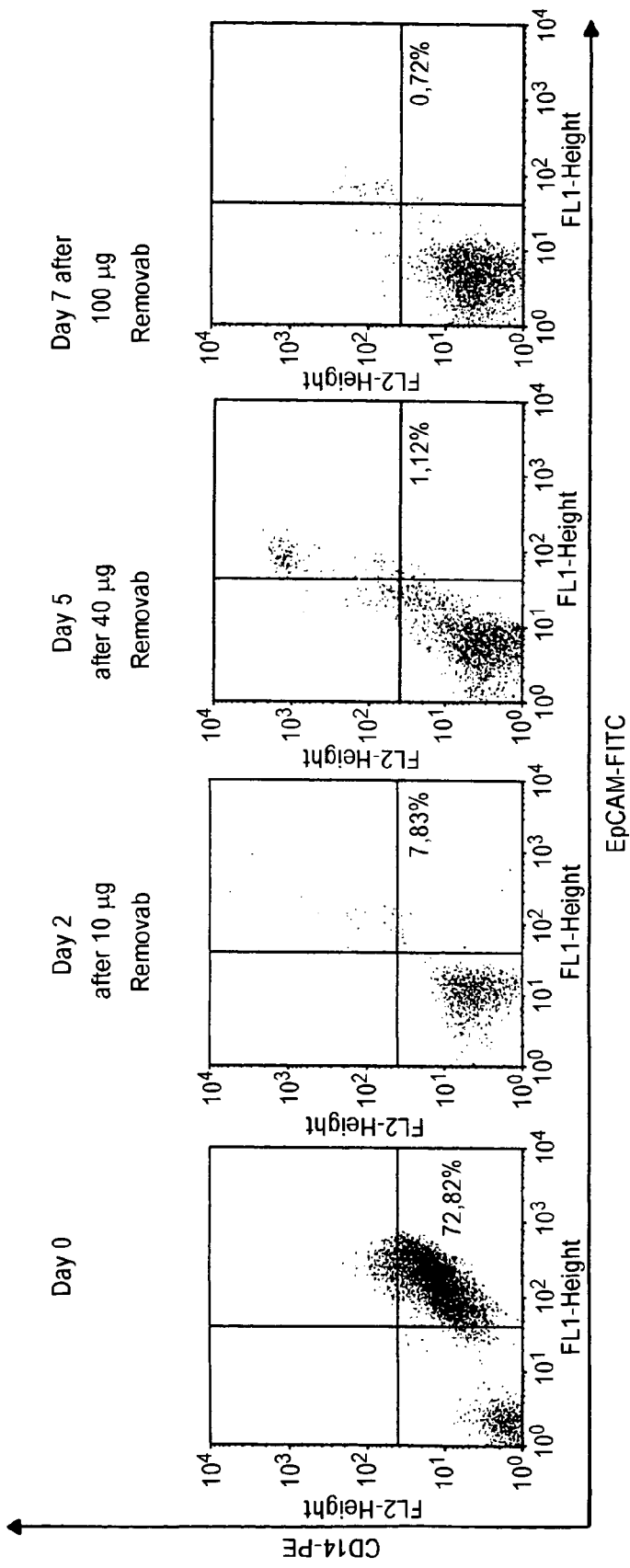
FIG. 4: Detection of EpCAM-positive tumor cells from the ascites liquid in flow cytometry during an antibody therapy.

In another patient suffering from mammary carcinoma and ascites formation also a peritoneal puncture was performed, ascites liquid (3 liters) was collected and the cells contained therein were analyzed by flow cytometry. For this purpose, detection antibodies against the tumor-associated antigen EpCAM and CD14 were used to be able to distinguish unspecific binding to Fc receptor-positive cells (of the detection antibodies) from a binding to tumor cells. As shown in FIG. 4 at the point of day 0 prior to therapy more than 70% of the cells which were detectable in the ascites liquid were EpCAM-positive tumor cells which, however, under therapy were reduced to 0.7%.

On day 0 after removal of the ascites liquid the patient received 10 µg of the anti-EpCAMxanti-CD3 REMOVAB® antibody (isotype combination: mouse IgG2axrat IgG2b) as well as on the following days 2 and 5 40 µg and 100 µg, respectively, of REMOVAB® intraperitoneally over a period of about 6 hours. On day 8 a combination of the Rexomab (anti-Her3/neuxanti-CD3; 100 µg) and REMOVAB® (50 µg) antibodies were applied intraperitoneally to the patient because in the flow cytometry also the tumor-associated antigen Her2/neu could be detected on the tumor cells (not shown).

Figure 5:
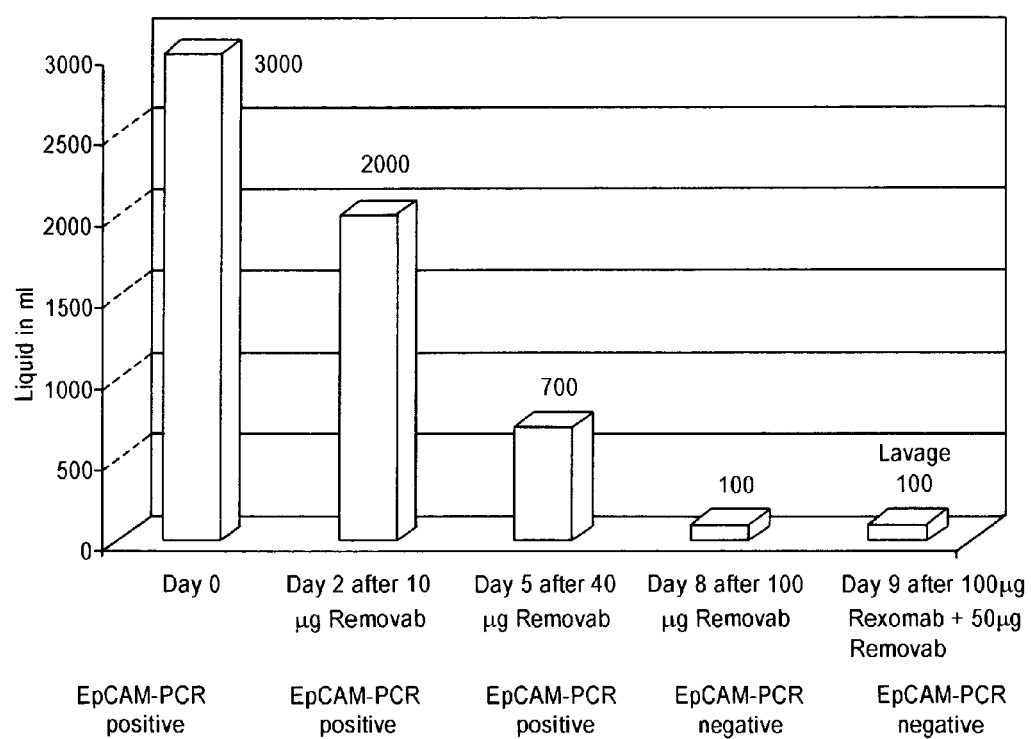
FIG. 5: Decrease of ascites liquid formed under therapy using the antibodies REMOVAB® (anti EpCAM×anti CD3) and REXOMAB (anti Her2/neu×anti CD3).

As depicted in FIG. 5 the new formation of liquid of the ascites continuously decreased under therapy and was completely abolished by the end of therapy.

The treatment was well tolerated. After the highest dose, however, a transient increase in liver values and a short-term fever occurred.

CONCLUSION

From these results it can be concluded that already a dose of 40 µg bsab has a certain anti-tumor effect and an activation and proliferation of immune effector cells is achieved. After an administration of 160 µg bsab no indication as to the presence of residual tumor cells in the peritoneal lavage of the first patient could be found even with very sensitive detection methods, and thus an effective destruction of the autologous tumor cells in the ascites liquid can be assumed. A similar effect could also be observed in the second patient after administration of 100 µg REMOVAB®. The tolerability of the doses administered was good, and only in one of the patients an increase in liver values or other negative side effects were observed. After the 250 µg dose (patient 1) and the 100 µg dose (patient 2) short-term fever (38.6° C.) occurred.

In this view, for future treatments for the destruction of tumor cells in the ascites and for inhibiting the new formation of ascites the following application of trifunctional bispecific antibodies results:

Day 0: 10 µg (starting dose to test for a hypersensitivity reaction against the foreign protein)
Day 2: 40 µg (activation and proliferation of immune cells)
Day 4: 200 µg (main dose for the destruction of the tumor cells)

Since at present there is no satisfactory treatment of malignant ascites which accompanies tumor diseases, the immune therapy by means of bsab is a novel and promising method.

The intraperitoneal immunetherapeutic treatment of ascites by means of trifunctional bsabs may also serve as a primary immunization for inducing a long-term anti-tumor immunity.

The abdominal cavity contains a number of immunological organs such as spleen, Peyer's plaques and a plurality of lymph nodes. Due to their interactions with tumor cells, T cells, and accessory cells (Zeidler et al., J. Immunol. 163: 1246, 1999; Zeidler et al., British J. Cancer 83:261, 2000), the trifunctional bsabs are capable of directing tumor material to the antigen-presenting system and to induce an infiltration of activated dendritic cells into the immunological organs.

These events are essential prerequisites for the induction of an immune response against the autologous tumor. To establish a long-term anti-tumor immune response and particularly to generate a functional polyclonal humoral and cellular immune response a secondary immunization is necessary. The secondary immunization can be performed subcutaneously or intradermally. As the autologous tumor material in the case of malignant ascites the tumor cells present therein may be prepared simply by means of puncture and may be used.

The invention claimed is:

1. A method for reducing or inhibiting the formation of ascites fluid in a subject, the method consisting of:
   (a) providing a subject having malignant ascites, wherein the malignant ascites comprises tumor cells; and
   (b) administering to the subject intraperitoneally three or more doses of a pharmaceutical preparation containing trifunctional bispecific antibodies as the sole therapeutically active agents, wherein:
      (i) the trifunctional bispecific antibodies comprise:
         (1) a first binding arm that binds to a T cell in the subject via CD3;
         (2) a second binding arm that binds to EpCAM on a tumor cell associated with malignant ascites in the subject;
         (3) an Fc portion that binds to an Fc receptor-positive cell in the subject that comprises an Fcγ receptor I, an Fcγ receptor III, or a combination thereof; and
         (4) isotype combination rat-IgG2b/mouse-IgG2a; and
      (ii) the administering is in several increasing doses, with the amount of the trifunctional bispecific antibodies present in the second dose being higher than the amount of the trifunctional bispecific antibodies present in the first dose, and the amount of the trifunctional bispecific antibodies present in the third and any subsequent doses being higher than the amount of the trifunctional bispecific antibodies present in the second dose;
   thereby reducing or inhibiting the formation of ascites fluid in the subject.

2. The method according to claim 1, wherein said first dose comprises 1 to 20 μg of the trifunctional bispecific antibodies, said second dose comprises 20 to 100 μg of the trifunctional bispecific antibodies, and said third and any subsequent doses each comprises 100 to 500 μg of the trifunctional bispecific antibodies.

3. The method according to claim 2, wherein the first dose comprises 5-10 μg of the trifunctional bispecific antibodies.

4. The method according to claim 2, wherein the second dose comprises 30-60 μg of the trifunctional bispecific antibodies.

5. The method according to claim 2, wherein the third dose, and any subsequent doses if present, comprises 100-300 μg of the trifunctional bispecific antibodies.

6. The method according to claim 1, wherein said administering step consists of administering 3 to 8 doses.

7. The method according to claim 6, wherein the administering step consists of administering 3 to 6 doses.

8. The method of claim 6, wherein an interval of about 2 to 3 days occurs between each dose.

9. The method according to claim 1, wherein said trifunctional bispecific antibodies induce tumor-reactive complement-binding antibodies and a humoral immune response in the subject.

10. The method according to claim 1, wherein binding of said trifunctional bispecific antibodies to the Fc receptor-positive cells induces or enhances Fc receptor-positive cell expression of at least one of CD40, CD80, CD86, ICAM-1, and LFA-3; secretion of a cytokine; or combinations thereof.

11. The method according to claim 10, wherein said cytokine is selected from the group consisting of IL-1, IL-2, IL-4, IL-6, IL-8, IL-12, INF-γ, and TNF-α.

12. The method according to claim 1, wherein binding of said trifunctional bispecific antibodies to Fc receptor-positive cells induces or enhances expression of a cytokine, a co-stimulatory antigen, or combinations thereof in the Fc-receptor-positive cell.

13. A method for reducing or inhibiting the formation of ascites or pleural effusion fluid, or a combination thereof, in a subject, the method consisting of administering to a subject having malignant ascites, pleural effusion, or a combination thereof comprising tumor cells, three or more doses of a pharmaceutical preparation containing trifunctional bispecific antibodies as the sole therapeutically active ingredients, wherein:
   (i) the amount of the trifunctional bispecific antibodies present in the second dose is higher than the amount of the trifunctional bispecific antibodies present in the first dose, and the amount of the trifunctional bispecific antibodies present in the third and any subsequent doses is higher than the amount of the trifunctional bispecific antibodies present in the second dose; and
   (ii) the trifunctional bispecific antibodies comprise a first binding arm that binds to a T cell in the subject via CD3, a second binding arm that binds to EpCAM on a tumor cell associated with malignant ascites or pleural effusion in the subject, and an Fc portion that binds to an Fc receptor-positive cell in the subject that comprises an Fcγ receptor I, an Fcγ receptor III, or a combination thereof; and
   (iii) the trifunctional bispecific antibodies are from the isotype combination rat-IgG2b/mouse-IgG2a,
   thereby reducing or inhibiting the formation of ascites or pleural effusion fluid, or the combination thereof, in the subject.

14. The method of claim 13, wherein an interval of about 48 to about 72 hours is present between administering each of the three or more doses.

* * * * *